US011690568B2

(12) United States Patent
Lee

(10) Patent No.: US 11,690,568 B2
(45) Date of Patent: Jul. 4, 2023

(54) APPARATUS, SYSTEM, AND METHOD FOR DETERMINING A LOCATION OF A STRUCTURE WITHIN A PATIENT'S VASCULATURE

(71) Applicant: THE GENERAL HOSPITAL CORPORATION, Boston, MA (US)

(72) Inventor: Kichang Lee, Newton, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 518 days.

(21) Appl. No.: 16/651,774

(22) PCT Filed: Oct. 1, 2018

(86) PCT No.: PCT/US2018/053738
§ 371 (c)(1),
(2) Date: Mar. 27, 2020

(87) PCT Pub. No.: WO2019/070572
PCT Pub. Date: Apr. 11, 2019

(65) Prior Publication Data
US 2020/0253543 A1    Aug. 13, 2020

Related U.S. Application Data

(60) Provisional application No. 62/566,903, filed on Oct. 2, 2017.

(51) Int. Cl.
*A61B 5/00* (2006.01)
*A61B 5/06* (2006.01)
(Continued)

(52) U.S. Cl.
CPC .............. *A61B 5/489* (2013.01); *A61B 5/063* (2013.01); *A61B 5/259* (2021.01); *A61B 5/283* (2021.01);
(Continued)

(58) Field of Classification Search
CPC ......... A61B 5/489; A61B 5/259; A61B 5/339; A61B 5/063; A61B 5/283; A61B 5/6852;
(Continued)

(56) References Cited

U.S. PATENT DOCUMENTS

| 2011/0270237 | A1* | 11/2011 | Werneth | ............... | A61B 5/6885 |
| | | | | | 606/20 |
| 2016/0067449 | A1* | 3/2016 | Misener | ............... | A61B 5/6852 |
| | | | | | 600/585 |
| 2017/0035323 | A1* | 2/2017 | Elberse | ................ | A61B 5/0006 |

OTHER PUBLICATIONS

"U S. Venous Access Catheter Market", Release date Oct. 1, 2010, https://store.frost.com/u-s-venous-access-catheter-market.html, last accessed Jan. 14, 2021.
(Continued)

*Primary Examiner* — Amanda K Hulbert
*Assistant Examiner* — Natasha Patel
(74) *Attorney, Agent, or Firm* — Tarolli, Sundheim, Covell & Tummino LLP

(57) ABSTRACT

A system for determining a location of a structure within a patients vasculature includes three or more pads adhered to the patients torso in a predetermined pad pattern. Each pad generates a pad electrical signal. A stylet has longitudinally spaced proximal and distal stylet ends, with at least one stylet electrode located proximate the distal stylet end. The stylet electrode receives the pad electrical signals and responsively generates a stylet electrical signal. A signal processor is operatively coupled for signal exchange with the stylet and to each of the pads via a selective electrical coupling. The signal processor compares the stylet electrical signal and at least two pad electrical signals to triangulate a position of the stylet electrode relative to each of the pads and responsively produce a triangulated position. The triangulated position is indicative of a position of the stylet electrode within the patients vasculature.

20 Claims, 9 Drawing Sheets

(51) Int. Cl.
    *A61M 25/01*     (2006.01)
    *A61B 5/259*     (2021.01)
    *A61B 5/283*     (2021.01)
    *A61B 5/339*     (2021.01)
(52) U.S. Cl.
    CPC ............ *A61B 5/339* (2021.01); *A61B 5/6852* (2013.01); *A61M 25/0102* (2013.01); *A61B 2562/0209* (2013.01); *A61M 2025/0166* (2013.01)
(58) Field of Classification Search
    CPC ............ A61B 2562/0209; A61B 5/318; A61B 2034/2072; A61M 25/0102; A61M 2025/0166
    USPC ........................................................ 600/374
    See application file for complete search history.

(56) References Cited

OTHER PUBLICATIONS

"Central Venous Catheters Market by Product Type (Tunneled Catheterss, Non-Tunneled Catheterss), By Design Type (Single Lumen, Double Lumen, Multi Lumen), By Composition Type (Polyurethane, Polyurethane/Polycarbonate, Silicone)—Growth, Share, Opportunities & Competitive Analysis, 2017-2025", Published 2017, https://www.credenceresearch.com/report/central-venous-catheters-market, last accessed Jan. 14, 2021.
PCT International Search Report and Written Opinion for corresponding International Application Serial No. PCT/US2018/053738, dated Jan. 2, 2019, pp. 1-16.

* cited by examiner

APPARATUS, SYSTEM, AND METHOD FOR DETERMINING A LOCATION OF A STRUCTURE WITHIN A PATIENT'S VASCULATURE

RELATED APPLICATION

This application is a national phase application of and claims priority from PCT International Patent Application PCT/US2018/053738, filed Oct. 1, 2018, which claims priority from U.S. Provisional Application No. 62/566,903, filed 2 Oct. 2017. The subject matter of each of the aforementioned applications is hereby incorporated by reference in its entirety.

TECHNICAL FIELD

This disclosure relates to an apparatus, system, and method for determining a location of a structure within a patient's vasculature and, more particularly, to a stylet for sensing electrocardiac characteristics of a patient and/or an apparatus, system, and method for placing a catheter within a patient's vasculature.

BACKGROUND

There are approximately 5,000,000 central lines placed in patients in US medical facilities each year. The rate of mechanical complications during the procedure ranges from 6% to 19%, which accounts for 250,000 to 1,000,000 complications annually. These complications often arise due to erroneous catheter navigation and placement, and include pneumothorax, artery puncture, thrombosis, infection, and delivery of medications to inappropriate sites causing corrosive injury. Moreover, the risk of mechanical complications has been found to increase by a factor of six, after the third failed insertion attempt.

Recently, several products using physiologic parameters or an external magnetic system to aid in the placement of peripherally inserted central catheters ("PICCs") without the use of chest X-Ray ("CXR") imaging have been commercialized to aid in bedside PICC placement. Several vascular navigation systems are commercially available to guide the PICC tip to the optimal location or confirm the tip utilizing real-time analysis of electrocardiogram ("ECG"), intravascular Doppler flow, and/or magnetic field strength. The magnetic field strength method operates along with a proprietary software algorithm that combines all received signals and translates them into symbols on the screen. However, accuracy and reliability of current techniques for PICC line guidance, including X-rays, external electromagnetic sensors, and intravascular sensors (i.e., ECG), are limited. Electromagnetic sensor techniques are inaccurate, as they determine only position relative to an external reference, rather than to a specific position within the vascular system. Intravascular sensors such as ECG's do not indicate the position a catheter tip in the blood vessel, but rather indicate the distance to the sino-atrial ("SA") node by tracking change in P-wave amplitude.

Current commercially available catheter tip confirmation systems have critical limitations. For instance, ECG P-waves of patients with abnormal cardiac conditions, such as atrial fibrillation, atrial flutter, severe tachycardia, and/or chronic obstructive pulmonary disorder, or pacemaker, may be nonexistent or indiscernible (i.e. no P-wave height growth). Thus, the current commercially available systems cannot be used to confirm tip location using the P-waves of ECGs. In addition, arm position and respiration phase (i.e., inspiration and expiration) can influence the tip location and lead to movement, resulting in a margin of error on the order of 2 cm, which may be unacceptable in many use environments. When the PICC with a stylet having electrode(s) at the tip is placed in the azygous vein or the systemic arteries near the heart, the P-wave pattern can be misleadingly similar to that seen with a desired placement at/near the cavoatrial junction ("CAJ"). All of these methods thus require a CXR to verify location of the catheter tip in the vasculature, which adds time, expense, and radiation exposure to the PICC line placement procedure.

SUMMARY

In an aspect of the present invention, a system for determining a location of a structure within a patient's vasculature is described. Three or more pads are adhered to the patient's torso in a predetermined pad pattern. Each pad is capable of generating a pad electrical signal having predetermined signal characteristics. A stylet has longitudinally spaced proximal and distal stylet ends. At least one stylet electrode is located proximate the distal stylet end. The stylet electrode is capable of receiving the pad electrical signals and responsively generating a stylet electrical signal. A signal processor is operatively coupled for signal exchange with the stylet and to each of the pads. The operative coupling between the signal processor and the stylet is a selective electrical coupling. The signal processor is capable of comparing the stylet electrical signal and at least two pad electrical signals to triangulate a position of the stylet electrode relative to each of the pads and responsively produce a triangulated position. The triangulated position is indicative of a position of the stylet electrode within the patient's vasculature.

In an aspect of the present invention, a method of placing a catheter within a patient's vasculature is described. Three or more pads are adhered to the patient's torso in a predetermined pad pattern. With each pad, a pad electrical signal having predetermined signal characteristics is generated. A stylet having longitudinally spaced proximal and distal stylet ends and at least one stylet electrode being located proximate the distal stylet end is provided. The pad electrical signals are received, and a stylet electrical signal is responsively generated with the stylet electrode. A signal processor is operatively coupled for signal exchange with the stylet and to each of the pads. The stylet electrical signal and at least two pad electrical signals are compared with the signal processor to triangulate a position of the stylet electrode relative to each of the pads. Responsive to the comparison between the stylet electrical signal and at least one pad electrical signal, a triangulated position indicative of a position of the stylet electrode within the patient's vasculature is produced. A user-perceptible indication of the triangulated position with respect to a target stylet electrode position is provided. An indication is provided to the user that the stylet electrode has reached a target position within the patient's vasculature responsive to the triangulated position becoming substantially equal to the target stylet electrode position. With the stylet electrode maintained at the target position, the proximal stylet end is disconnected from the signal processor. With the stylet disconnected from the signal processor and the stylet electrode maintained at the target position, the stylet is inserted into a lumen of the catheter. The catheter is passed over the stylet into the patient's vasculature to a predetermined catheter position.

In an aspect of the present invention, a stylet for sensing electrocardiac characteristics of a patient is provided. A stylet body has longitudinally spaced proximal and distal stylet ends. At least one bipolar stylet electrode is located on the stylet body proximate the distal stylet end. The bipolar stylet electrode is capable of generating a stylet bipolar electrical signal responsive to sensed electrical activity within the patient's body. At least one unipolar stylet electrode is located on the stylet body, longitudinally interposed between the bipolar stylet electrode and the proximal stylet end. The unipolar stylet electrode is capable of generating a stylet unipolar electrical signal responsive to sensed electrical activity within the patient's body. At least two controller contacts are located on the stylet body proximate the proximal stylet end. Each controller contact is in electrical connection with a selected one of the at least one bipolar stylet electrode and the at least one unipolar stylet electrode. The at least two controller contacts are capable of selective electrical connection with a signal processor for transmitting a respective stylet bipolar electrical signal and stylet unipolar electrical signal to the signal processor.

BRIEF DESCRIPTION OF THE DRAWINGS

For a better understanding, reference may be made to the accompanying drawings, in which.

DESCRIPTION OF ASPECTS OF THE DISCLOSURE

Figure 1:
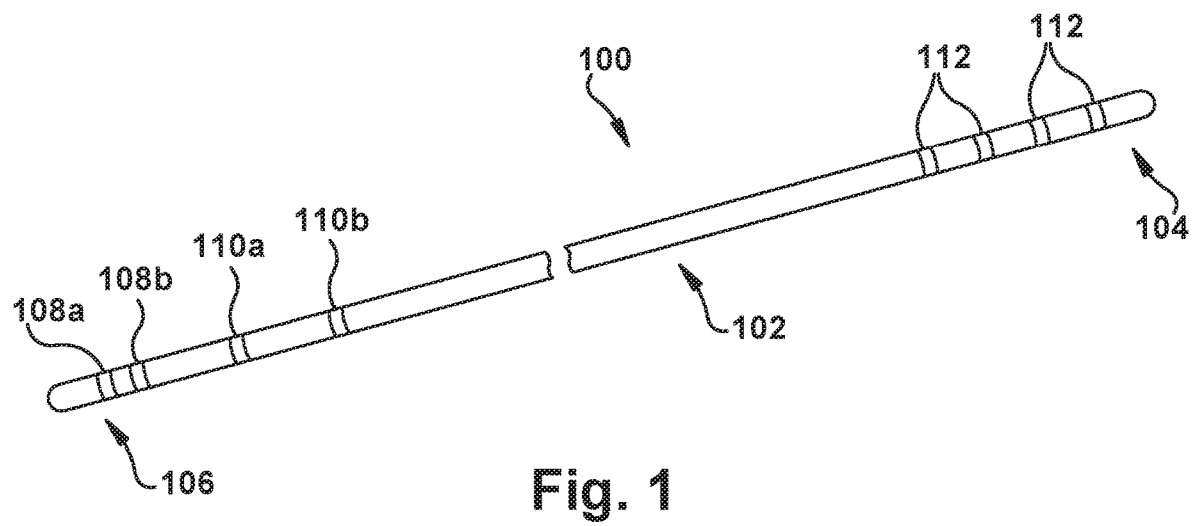
FIG. 1 is a side view of an apparatus according to an aspect of the invention.

Unless defined otherwise, all technical and scientific terms used herein have the same meaning as is commonly understood by one of skill in the art to which the present disclosure pertains.

As used herein, the term "patient" can be used interchangeably with the term "subject" and refer to any warm-blooded organism including, but not limited to, human beings, pigs, rats, mice, dogs, goats, sheep, horses, monkeys, apes, rabbits, cattle, farm animals, livestock, etc.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

FIG. 1 depicts a stylet 100 for sensing electrocardiac characteristics of a patient. The stylet 100 comprises a stylet body 102 with longitudinally spaced proximal and distal stylet ends 104 and 106, respectively. The stylet body 102 may have a cross-sectional diameter, for example, less than about 0.48 mm, or, more specifically, between about 0.015-0.020 mm for some use environments—e.g., when the stylet 100 is later passed down a catheter lumen with a 1 French internal size. (It should be noted that the catheter could be of the single-lumen or multi-lumen types.) The stylet 100, and portions thereof, however, may have any desired dimensions for a particular use environment.

At least one bipolar stylet electrode 108 is located on the stylet body 102 proximate the distal stylet end 106. The bipolar stylet electrode 108 is capable of at least partially generating a stylet bipolar electrical signal responsive to sensed electrical activity within the patient's body—it should be understood that this stylet bipolar electrical signal is indicative of electrode-sensed electrical activity within the body, such as contributing to an ECG lead reading.

In the example stylet 100 shown in the Figures and described here, there are two bipolar stylet electrodes 108a and 108b. The two bipolar stylet electrodes 108a and 108b may be spaced apart in the range of about 2-7 mm apart, more specifically about 3-6 mm apart, and more specifically about 3.5-5.5 mm apart, for use in an adult patient. Similarly, the two bipolar stylet electrodes 108a and 108b may be spaced apart in the range of about 0.1-4 mm apart, more specifically about 0.25-3 mm apart, and more specifically about 0.5-2.5 mm apart, for use in a child patient.

At least one unipolar stylet electrode 110 (which, similarly, may be used in combination with another electrode in a may be located on the stylet body 102, longitudinally interposed between the bipolar stylet electrode(s) 108 and the proximal stylet end 104. The unipolar stylet electrode 110 is capable of generating a stylet unipolar electrical signal responsive to sensed electrical activity within the patient's body—it should be understood that this stylet unipolar electrical signal is indicative of electrode-sensed electrical activity within the body, such as contributing to an ECG lead reading.

For the avoidance of doubt, it should be noted that each bipolar stylet electrode 108 is capable of being used alone as a unipolar stylet electrode 110 when desired, but will be referenced herein as being primarily used in a bipolar manner, for clarity. Similarly, the unipolar stylet electrodes 110 could be used in various combinations with each other and/or with the bipolar stylet electrodes 108 in a bipolar manner, but will be referenced herein as being primarily used in a unipolar manner, for clarity. Both the bipolar and unipolar stylet electrodes 108 and 110 may be used to receive cardiac electrical activity signals (low frequency) and/or high frequency navigation signals, as described below with respect to the passive and active usage modes, respectively, for the stylet 100. If the procedure room is electrically noisy and/or patient physical conditions, such as extremely obesity, edema, and/or skin burn conditions, impede normal ECG readings, bipolar signal processing (using signals from any desired one or more bipolar and/or unipolar stylet electrodes 108 and 110) can be used to navigate and confirm the location of the stylet 110.

In the example stylet 100 shown in the Figures and described here, there are two unipolar stylet electrodes 110a and 110b. For some use environments of the stylet 100, a distalmost one of the unipolar stylet electrode(s) 110 may be spaced in the range of about 0.1-4 cm, more specifically about 0.25-3 cm, and more specifically about 0.5-2.5 cm proximal to a proximalmost one of the bipolar stylet electrode(s) 108. The two unipolar stylet electrodes 110a and 110b, when present, may be spaced apart in the range of about 0.1-4 cm apart, more specifically about 0.25-3 cm apart, and more specifically about 0.5-2.5 cm apart.

The relative and absolute spacing of any of the bipolar and unipolar electrodes 108 and 110 along the stylet 100 may be selected for a particular use environment by one of ordinary skill in the art during implementation of the apparatus(es) and method(s) shown and described herein. For example, the bipolar and/or unipolar electrodes 108 and 110 could be spaced for a particular patient according to expected, average, and/or measured cardiac anatomy, to facilitate obtaining electrocardiogram ("ECG") or other electrical signal results as desired for any purpose, including stylet navigation and/or confirmation, as will be discussed below in detail.

As just alluded to, the sensed electrical activity may be naturally occurring cardiac electrical activity, and the stylet unipolar and bipolar electrical signals are ECG signals. ECG signals, as referenced here, include at least one of intravascular ECG signals and external ECG signals, with unipolar and/or bipolar varieties of either/both. Additionally or alternatively, the sensed electrical activity may be artificially imposed signal waveform electrical activity, and the stylet unipolar and bipolar electrical signals are indicative of a strength of the signal waveform electrical activity at the respective unipolar or bipolar stylet electrode 110 or 108.

The bipolar and unipolar stylet electrode(s) 108 and 110 may be configured in any desired manner. However, it is contemplated that at least one of the unipolar stylet electrode(s) 110 and/or the bipolar stylet electrode(s) 108 may include a band, which could be of any suitably electrically conductive metal such as, but not limited to silver, copper, gold, or the like. For example, in some use environments, the electrode could comprise a platinum-iridium band extending circumferentially around the stylet body 102. The platinum-iridium band, or any other electrode 108 or 110 structure, may be substantially flush with directly longitudinally adjacent portions of the stylet body 102, such that a substantially smooth outer profile is present along the length of the stylet 100. It may be particularly desirable to have a substantially smooth outer profile or surface when the stylet 100 is used within a lumen of a catheter or other sleeve-type structure into which the stylet 100 is inserted and, potentially, is moved within or with respect to.

At least two controller contacts 112 may be located on the stylet body 102 proximate the proximal stylet end 104. Each controller contact 112, when present, is in electrical connection with a selected one of the bipolar stylet electrode(s) 108 and the unipolar stylet electrode(s) 110. The controller contacts 112 are capable of selective electrical connection with a signal processor 214, as shown in FIG. 2, for transmitting a respective stylet bipolar electrical signal and stylet unipolar electrical signal to the signal processor 214.

Figure 2:
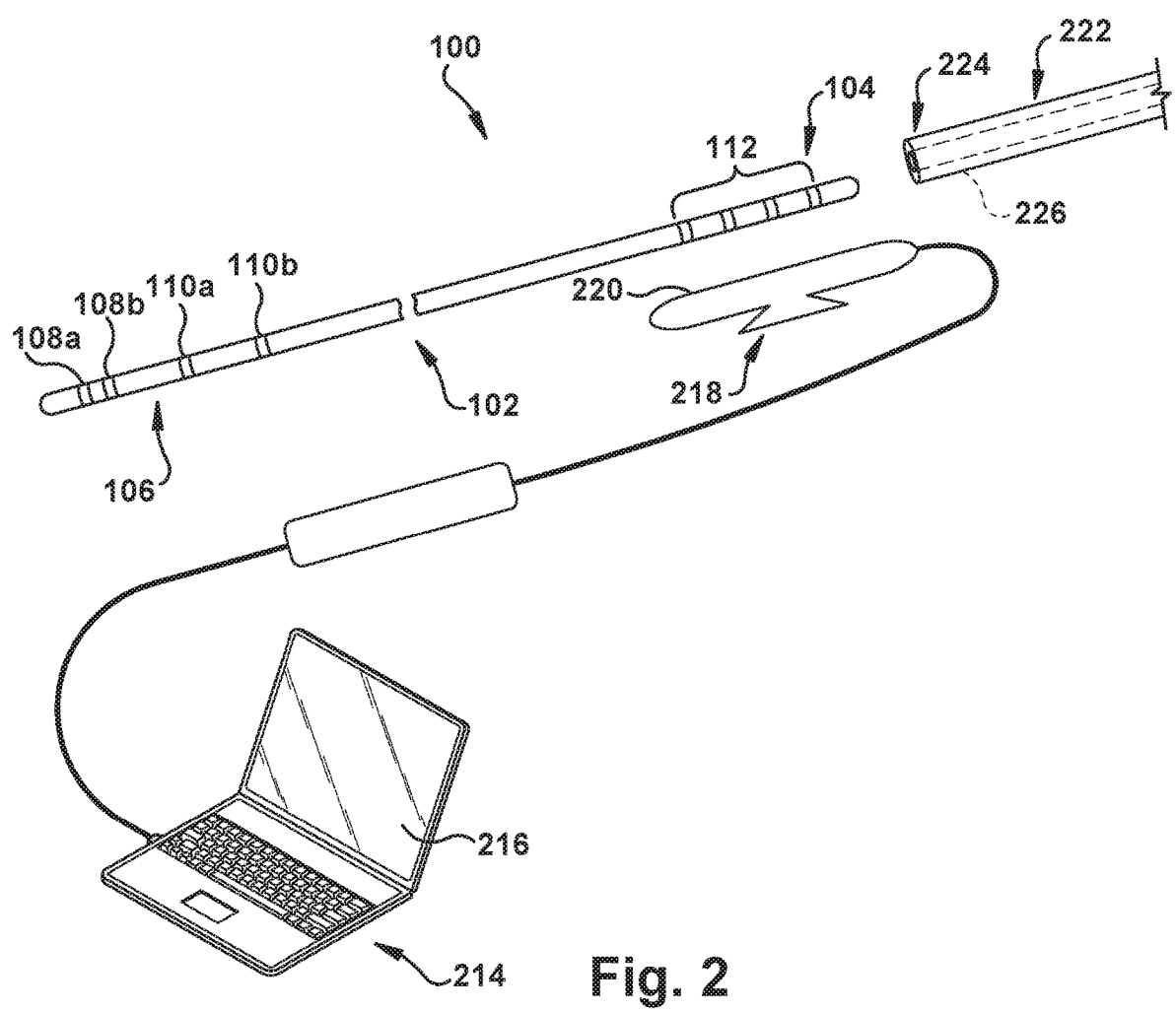
FIG. 2 is a schematic view of the apparatus of FIG. 1 in an example use environment.

With reference to FIG. 2, a stylet connector 218 could effectuate the selective electrical coupling between the signal processor 214 and the stylet 100. The stylet connector 218 may include an annular coupler 220, which interfaces with the controller contacts 112 for electrical signal transmission (including electrical power transmission) therewith in any desired manner. For example, the annular coupler 220 could include one or more slip rings, keyed connectors, plug-and-socket connectors, bayonet connectors, jacks, alligator clips, wire quick connectors, or any other desired connection structures for placing the controller contacts 112 and the signal processor 214 into selective operative connection.

As an example, and as shown in FIG. 2, the signal processor 214 could be a desired computing device such as, but not limited to, a laptop computer, a desktop computer, a tablet, a smartphone, a personal digital assistant, a dedicated stylet-interface station, any other type of computing device, or a combination thereof. The signal processor 214 may include, or be operatively connected to, any desired type of user-perceptible display device 216 such as, but not limited to, a visual interface, an audible interface, a tactile interface, any other interface or component for producing a user-perceptible signal, or any combination thereof. For example, the user-perceptible display device 216 shown in FIG. 2 is a computer monitor.

It is also contemplated that the user-perceptible display device 216 could make available to the user a perceptible representation of the respective stylet bipolar electrical signal and stylet unipolar electrical signal, in real-time and or on a delayed basis, with or without signal processing as desired. In this manner, the user (e.g., a medical professional) could personally review and interpret the signal data as desired. This may be helpful when the user is experienced with signal (e.g., ECG) interpretation.

However, the user-perceptible display device 216 could also or instead provide the user with a simpler indication, for any desired reason, such as by providing the user with an alert (audible, visual, tactile, and/or any other type) when one or more types of signal data meets a predetermined condition. The predetermined condition could be, for example, entering or exiting a predetermined signal range, becoming in phase with a predetermined reference signal, and/or any other condition of potential interest to the user.

When the stylet 100 is being used to confirm venous access to a particular portion of the patient's cardiovascular system, for example, the user-perceptible display device 216 could sound a tone or flash a light when an ECG signal from at least one of the bipolar and unipolar stylet electrodes 108 and 110 substantially matches an ECG reading which would be expected when that bipolar or unipolar stylet electrode 108 or 110 is located in the target area of the patient's cardiovascular system. The user could also or instead make such comparison/analysis manually, such as by reference to a visual representation of the ECG signal from the bipolar or unipolar stylet electrode 108 or 110 in combination with the user's knowledge of the expected ECG signal at that target area. Using the stylet bipolar electrical signal data and/or stylet unipolar electrical signal data, the user can accordingly determine and/or confirm a location of the respective bipolar or unipolar stylet electrode 108 or 110 (and thus, by extension, the location of the stylet 100 in general) within the patient's cardiovascular system.

The location confirmation, indication, and/or verification ability described above may be very useful in any of a number of patient treatment and/or monitoring tasks in a medical setting. It may be desirable to place a PICC, central venous catheter ("CVC") or other central venous line, for example, in a "bedside" setting and/or without the use of a confirmatory CXR. The below description presumes a PICC line placement task, but one of ordinary skill in the art will be able to use the stylet 100 and other described structures/methods for any desired medical task.

During PICC line placement, it is usually desirable to place the distalmost end of the catheter (shown schematically at 222 in FIG. 2) in the lower third of the superior vena cava ("SVC"), near the junction of the SVC and the right atrium ("RA"), which is known as the cavoatrial junction ("CAJ"). In order to do so, the stylet 100 may be threaded through the patient's peripheral vasculature (e.g., cephalic, basilic, or brachial vein), accessed in any suitable manner (e.g., via a Seldinger or modified Seldinger technique), and to the SVC. At least one of the stylet bipolar electrical signal and stylet unipolar electrical signal can be monitored to track the stylet's 100 progress through the patient's vasculature. That is, since the expected ECG patterns (e.g., the bipolar and/or unipolar cardiac electrical signal activity patterns) change in a known manner at different anatomical locations within the cardiac system, the user could monitor the stylet bipolar electrical signal(s) and/or stylet unipolar electrical signal(s) to indicate, indirectly, where in the cardiovascular system the corresponding bipolar or unipolar stylet electrode 108 or 110 is located.

Stated differently, the stylet 100 could be advanced through the vasculature and the stylet bipolar electrical signal(s) and/or stylet unipolar electrical signal(s) could be monitored. When the distalmost one of the bipolar stylet electrodes 108a starts to give an ECG stylet bipolar electrical signal indicative of a location within the SVC, the user could gradually feed the stylet 100 forward until the stylet bipolar electrical signal from that distalmost bipolar stylet electrode 108a changes into an ECG pattern correlated with a position within the RA. The user can then either edge the stylet 100 backward slightly, to place the distal stylet end 106 just outside the CAJ, or can leave the stylet 100 in place with the distalmost bipolar stylet electrode 108a giving a RA-associated stylet bipolar electrical signal and at least one more proximally located bipolar stylet electrode 108b giving a stylet bipolar electrical signal correlated with a location in the SVC. Thus, some combination of the two bipolar stylet electrodes 108a and 108b and the unipolar electrode(s) 110 will likely be "bracketing" the desired location for the catheter distal end 224 to achieve in the final PICC placement. The stylet 100 will then be maintained in position to guide the PICC line insertion.

Through markings along the stylet body 102, a relative length of the stylet 100 remaining outside the patient's body, and/or any other indication or method, the user will know the length of PICC line needed for installation of desired. That length of catheter 222 tubing can be cut. The proximal stylet end 104 is then temporarily removed from the stylet connector 218 and inserted into a lumen 226 of the catheter 222. The catheter 222 is then passed over the stylet 100 and threaded through the patient's vasculature, toward the CAJ. Once the entire length of the catheter 222 has been advanced onto the stylet 100, the stylet connector 218 can once again be operatively coupled to the proximal stylet end 104 (and the controller contacts 112), and signal monitoring of the stylet bipolar electrical signal(s) and/or stylet unipolar electrical signal(s) can recommence.

The catheter 222 will tend to block, damp, or otherwise obscure/alter the stylet bipolar electrical signal(s) and/or stylet unipolar electrical signal(s) as the catheter 222 passes over the bipolar and unipolar stylet electrodes 108 and 110. Therefore, the user can fairly accurately track a location within the vasculature of the catheter distal end 224, optionally through the use of bipolar and/or unipolar stylet electrodes 108 and 110 spaced along a majority of the stylet body 102 as well as those pictured near the distal stylet end 106 in the Figures. Once the catheter distal end 224 is deemed to have passed over one or more selected bipolar and/or unipolar stylet electrodes 108 and 110—e.g., has passed over the bipolar stylet electrode 108b but not the distalmost bipolar stylet electrode 108a—the user can presume that the catheter distal end 224 is located in a desired target area at/near the CAJ.

The catheter 222 can then be held in place, the stylet 100 can be withdrawn proximally from within the catheter lumen 224, and the remainder of the PICC line installation procedure can be conducted with confidence as to the catheter distal end 224 location relative to the heart. To facilitate use of the stylet 100 as described, or in any other suitable manner for a particular use environment, any desired number of bipolar and/or unipolar stylet electrode(s) 108 and 110 can be placed in any desired position(s) along the stylet body 102, responsive to actual or expected patient anatomical characteristics, ECG or other signal configurations, patient conditions, patient phenotypes, patient physical attributes (such as, but not limited to, obesity, edema, general health), and/or any other desired factors.

As described above, the stylet 100 could be used alone to confirm or verify the location of the distal stylet end 106 at a desired target location, such as near the CAJ. It is contemplated, though that a stylet 100 could also or instead be used as a part of a system for determining a location of a structure within a patient's vasculature, and/or for navigating that structure to a desired target location within the patient's cardiovascular system. (The above description of the stylet 100 will not be generally repeated below with reference to the system and method, though is incorporated by reference for brevity.)

Figure 3:
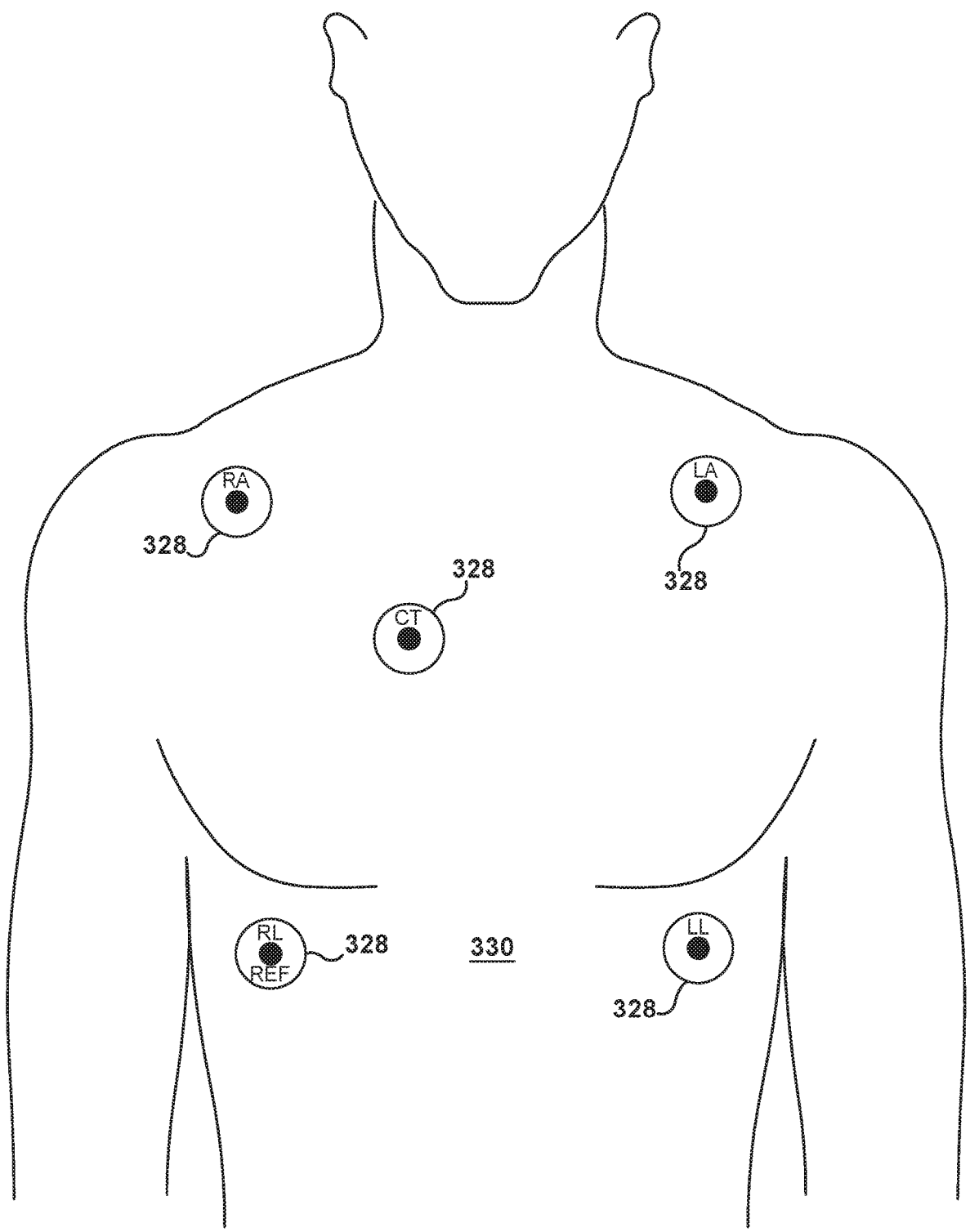
FIG. 3 depicts an example use environment for an aspect of the invention.

In such a system, any desired number of pads (shown at 328 in FIG. 3) can be adhered to the patient's torso 330 in a predetermined pad pattern. For example, five pads 328 adhered to the patient's torso 330 in an X-shaped pattern in the Figures, with a center CT pad located substantially at the intersection of imaginary diagonal lines running between the right arm RA and left leg LL pads, and between the left arm LA and right leg RL pads. It should be noted that when a unipolar stylet electrode 110 is placed under the area of the center CT pad, no ECG signal will be generated.

Signal strengths and patterns from surface cardiac Leads I, II, and III, intravascular cardiac electrical activity signals between the bipolar and/or unipolar stylet electrodes 108 and 110, and/or the pads 328 can be compared and used to navigate and confirm the stylet 100 location.

The general ECG bipolar surface lead configurations include:
  LEAD I: LA-RA
  LEAD II: LL-RA
  LEAD III: LL-LA Additional ECG bipolar surface lead configurations include:
  LEAD IV: CT-RA
  LEAD V: LL-CT
  LEAD VI: CT-LA Pads 328 include RA (right arm), LA (left arm), LL (left leg), CT (center chest) (which may be placed on the body surface at an area estimated to be near the right atrium), and RL (right leg) which may be used as a system reference.

Intravascular ECG bipolar surface lead configurations include:
  Intravascular LEAD I: bipolar and/or unipolar stylet electrodes 108 and 110-RA
  Intravascular LEAD II: LL-bipolar and/or unipolar stylet electrodes 108 and 110
  Intravascular LEAD III: bipolar and/or unipolar stylet electrodes 108 and 110-LA
  Intravascular LEAD IV: CT-bipolar and/or unipolar stylet electrodes 108 and 110

Any desired number, type(s), configurations, and placements of pads 328 may be provided for a particular use environment by one of ordinary skill in the art. However, it is contemplated that generally a system will include three or more pads 328 for triangulation tasks, as described below. While no particular placement of the pads 328 relative to each other and to features of the patient's anatomy is required for the system, the pads 328 will normally be adhered to the patient's torso 330 in a fixed manner during each complete episode of system use, to serve as substantially constant landmarks.

Each pad 328 is capable of generating a pad electrical signal having predetermined signal characteristics. For example, in a "passive" version of the system, at least one pad 328 senses naturally occurring electrical heart activity and responsively generates an electrocardiogram ("ECG") signal as the pad electrical signal.

As another example, in an "active" version of the system, at least one pad 328 generates a signal waveform having a predetermined frequency, optionally under control or direction from the signal processor 214. The signal waveform may be of a high frequency type (e.g., more than 1000 Hertz), for example. In some use environments, several specialized high-frequency signals (without any common harmonics) could be infused into the body via the pads 328. As cardiac activity signals are low frequency signals and the signal waveforms are high frequency signals, the signal processor 214 (potentially including artificial intelligence and/or neural network) can distinguish the various signals received by the bipolar and/or unipolar stylet electrodes 108 and 110.

Regardless of whether the system is active or passive, the stylet 100 includes at least one stylet electrode 108/110 (which may be of the bipolar or unipolar type(s) as described above). The stylet electrode 108/110 is capable of receiving the pad electrical signals generated by each pad 328 and responsively generating a stylet electrical signal. The signal processor 214 is operatively coupled for signal exchange with the stylet 100 and to each of the pads 328. The operative coupling between the signal processor 214 and the stylet 100 may be a selective electrical coupling, such as via the stylet connector 218 described above.

The signal processor 214 is capable of comparing the stylet electrical signal and at least two pad electrical signals to triangulate a position of the stylet electrode 108/110 relative to each of the pads 328 and responsively produce a triangulated position. This triangulation can be done in any desired manner such as, but not limited to, fast Fourier transforms, time-of-flight calculations, cost mapping, and/or any other desired algorithmic manipulations. The triangulated position may be calculated, for example, responsive to a comparison between the strengths of at least two pad electrical signals relative to the stylet electrical signal. Any desired weighting can be given to any factors in performing the triangulation calculations including, but not limited to, physical characteristics of the patient, configuration characteristics of the pad(s) 328, and/or strength of the pad electrical signal(s). In the passive version of the system, the ECG signals between pairs of pads 328 (i.e., along the ECG "leads") are known. In the active version of the system, the signal processor 214, or another controller (not shown), can modulate or otherwise differentiate the signal waveforms from each pad 328 to assist the system with distinguishing the signal waveforms being detected by each stylet electrode 108/110.

The triangulated position is indicative of a position of the stylet electrode 108/110 within the patient's vasculature. Particularly when multiple stylet electrodes 108/110 are provided, the stylet 100 location and orientation within the patient's vasculature can be extrapolated once the positions of the stylet electrodes 108/110 are known. As a result, the stylet 100 position relative to a target area (e.g., the CAJ) within the patient's cardiovascular system can be tracked and employed by the user to inform the insertion process of the stylet 100 into the patient's body. In other words, the signal processor 214 can process cardiac activity signals from some combination of pads 328 and at least one of the bipolar and/or unipolar stylet electrodes 108 and 110 to detect the location of the stylet 100 (e.g., the distal stylet end 106) and display that location information in a useful form on the user-perceptible display device 216 to assist the user with navigating the stylet 100, and by extension the catheter 222, within the patient's body.

Figure 4:
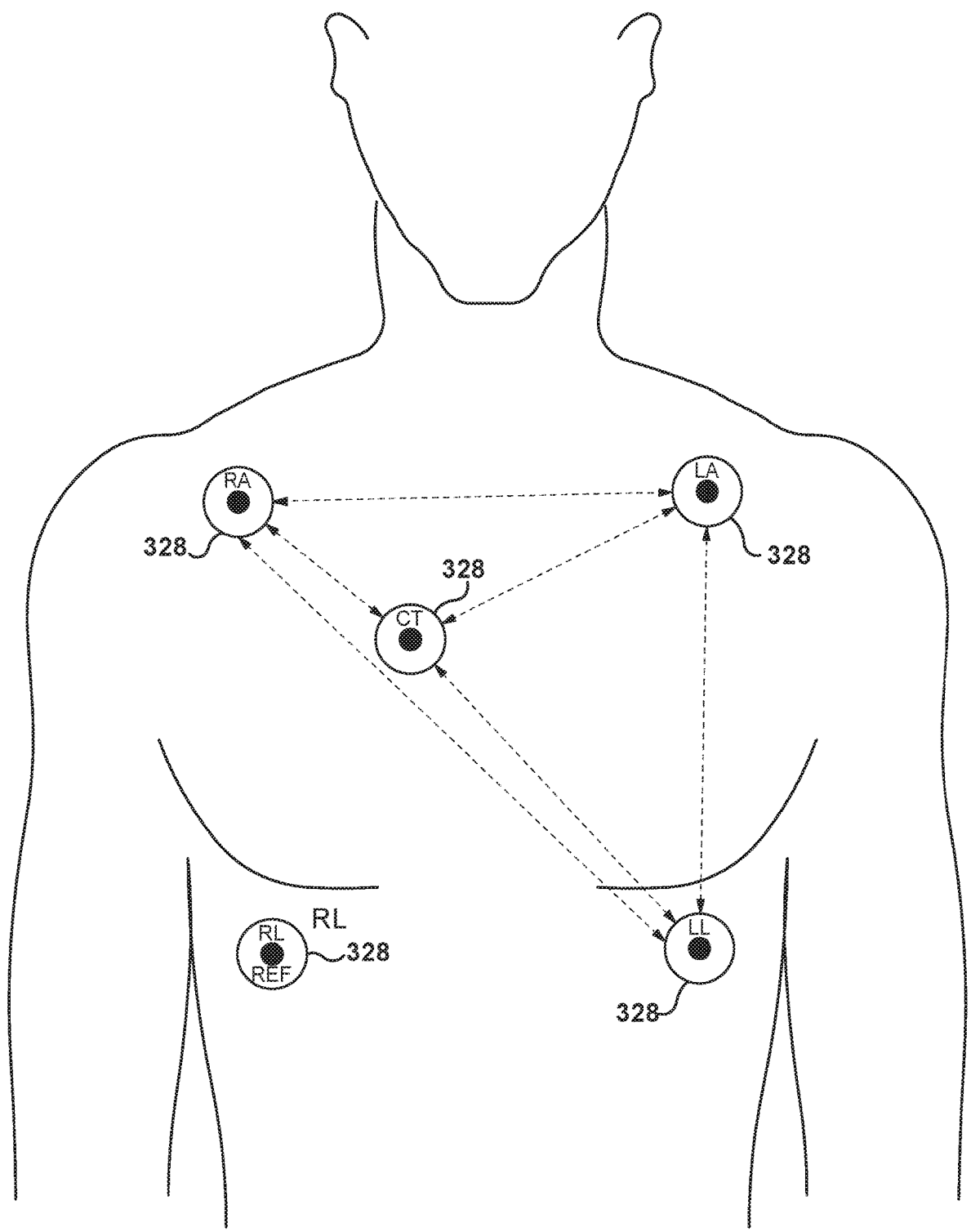
FIG. 4 depicts example signal flow in the use environment of FIG. 3.
Figure 5:
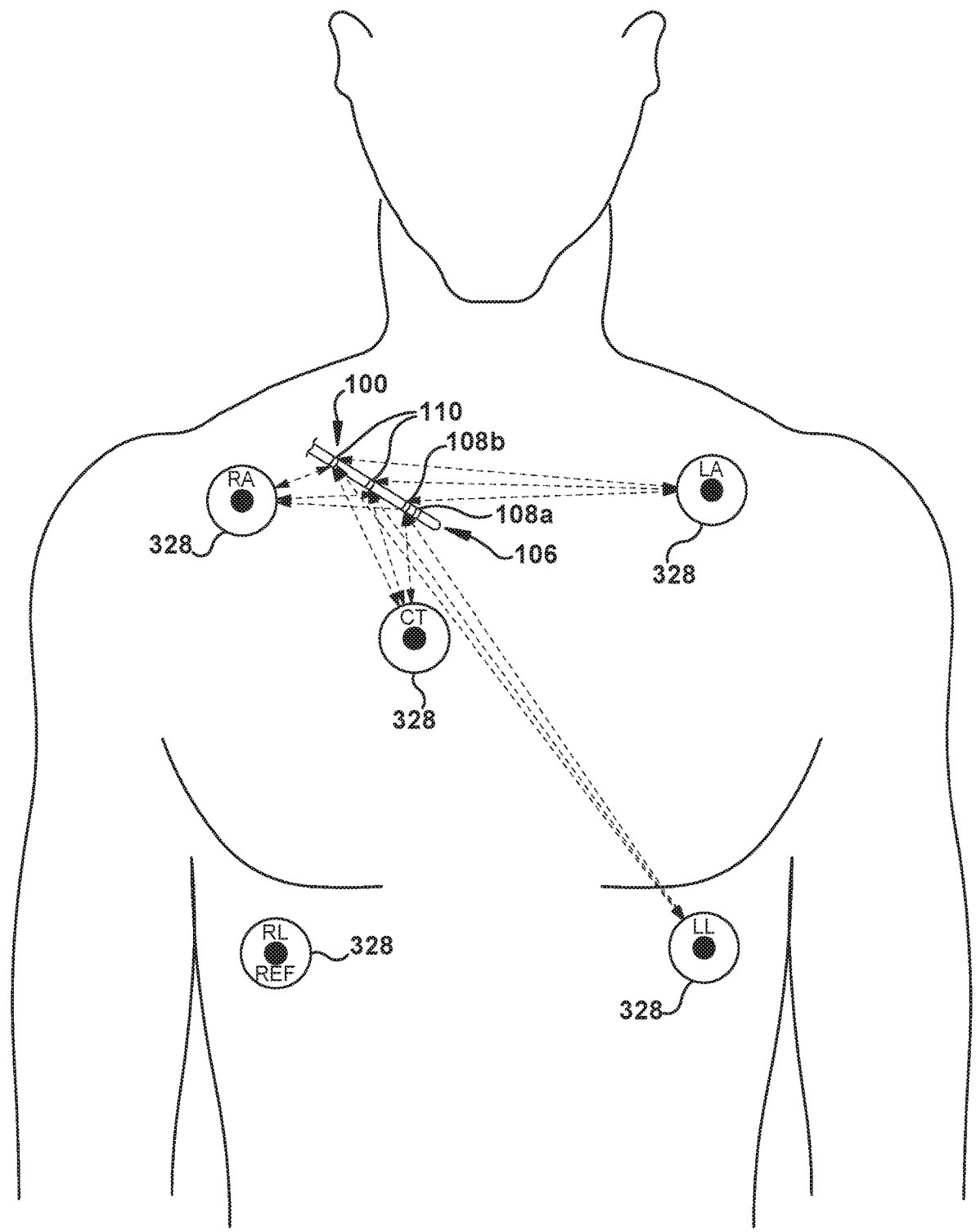
FIG. 5 schematically depicts interaction of the apparatus of FIG. 1 with the use environment of FIG. 3.

FIGS. 4-5 schematically depict operation of the triangulation portion of both the active and passive systems including the stylet 100. As shown in FIG. 4, the distance and/or signal characteristics between each of multiple pairs of pads 328 are "known" by the signal processor 214, in any suitable manner. Turning to FIG. 5, the stylet 100 has entered the patient's torso 330 vasculature and is traveling through the SVC toward the RA. The distance and/or signal characteristics between each pad 328 and each stylet electrode 108/110 are "known" by the signal processor 214, in any suitable manner. For each stylet electrode 108/110, knowing the distances between that particular stylet electrode 108/110 and each of at least two pads 328 allows the signal processor 214 to determine a location of that particular stylet electrode 108/110 relative to each of those pads 328, and thus extrapolate the position of the stylet electrode within the body. Since the CT (center) pad 328 is right over the patient's heart, the signal processor 214 can then accurately calculate the motion vector needed to advance the stylet 100 toward the heart. It should be noted that the CT (center) signal may be useful to help confirm a location of the distal stylet end 106 in the vasculature of patients with conditions including, but not limited to, atrial fibrillation, flutter, and tachycardia.

It should be noted that the signal processing algorithms used in either the active or passive system may rely upon any desired number and type of the "known" distances shown via dashed lines in FIGS. 4-5, and upon any other available data—e.g., patient imaging scans—for a particular use environment. One of ordinary skill in the art will readily be able to design suitable algorithms, based at least partially upon the principles outlined herein, for a particular use environment of the system.

Figure 6:
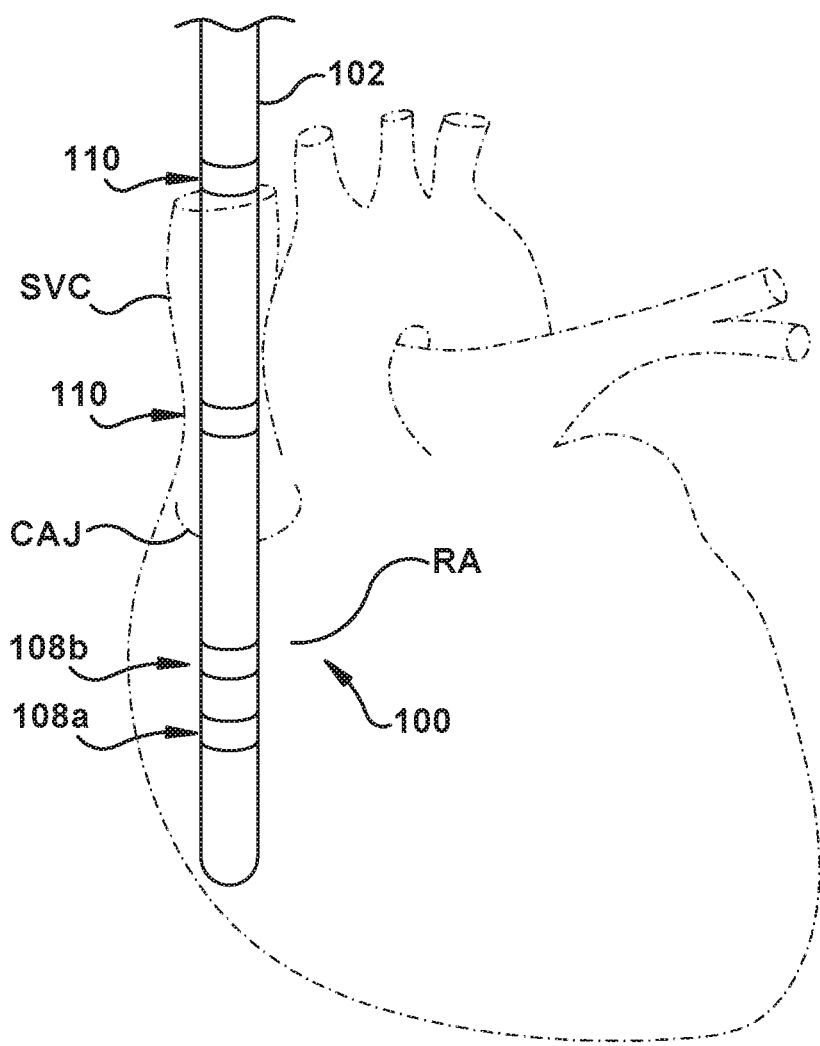
FIG. 6 schematically depicts the apparatus of FIG. 1 in an example patient heart.
Figure 7:
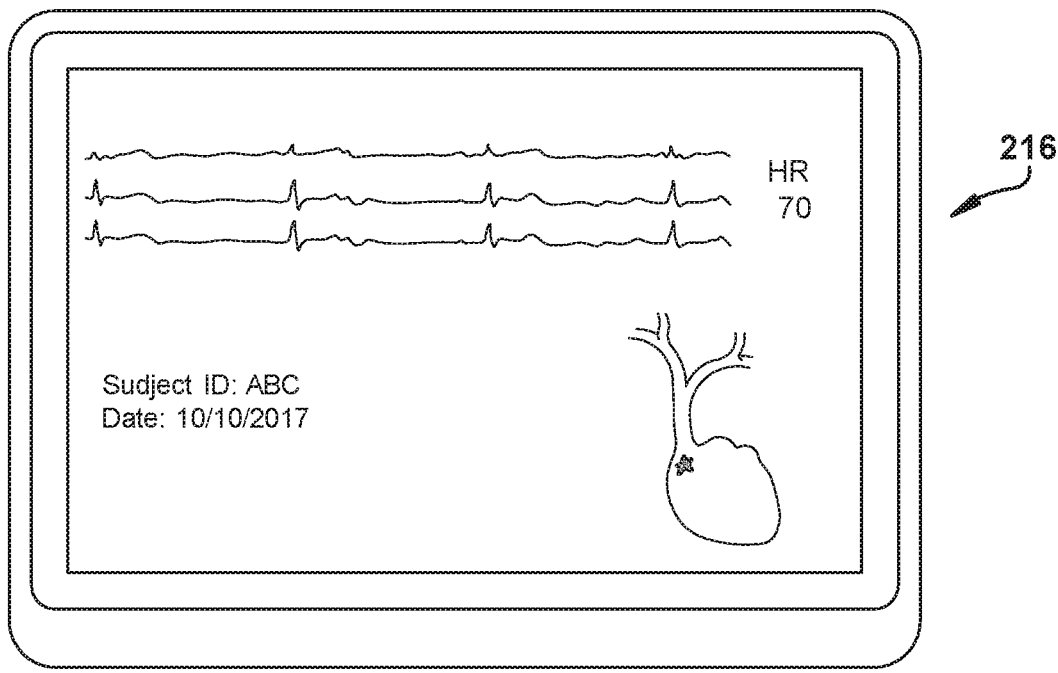
FIGS. 7-10 depict various user-perceptible displays during use of the apparatus of FIG. 1 in the use environment of FIG. 3.
Figure 8:
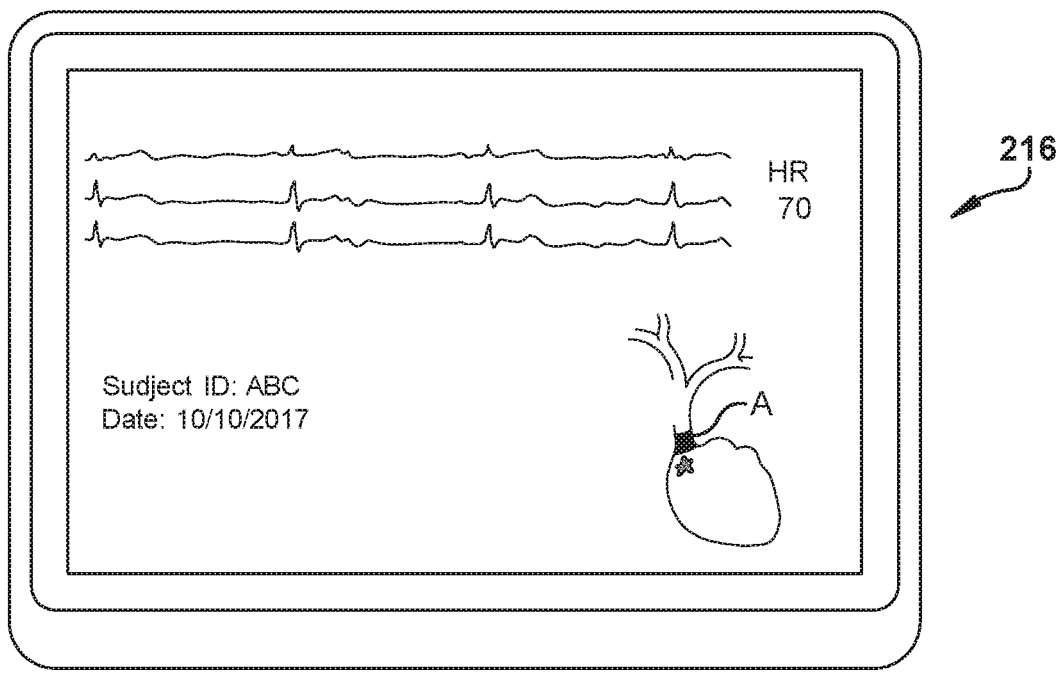
Figure 9:
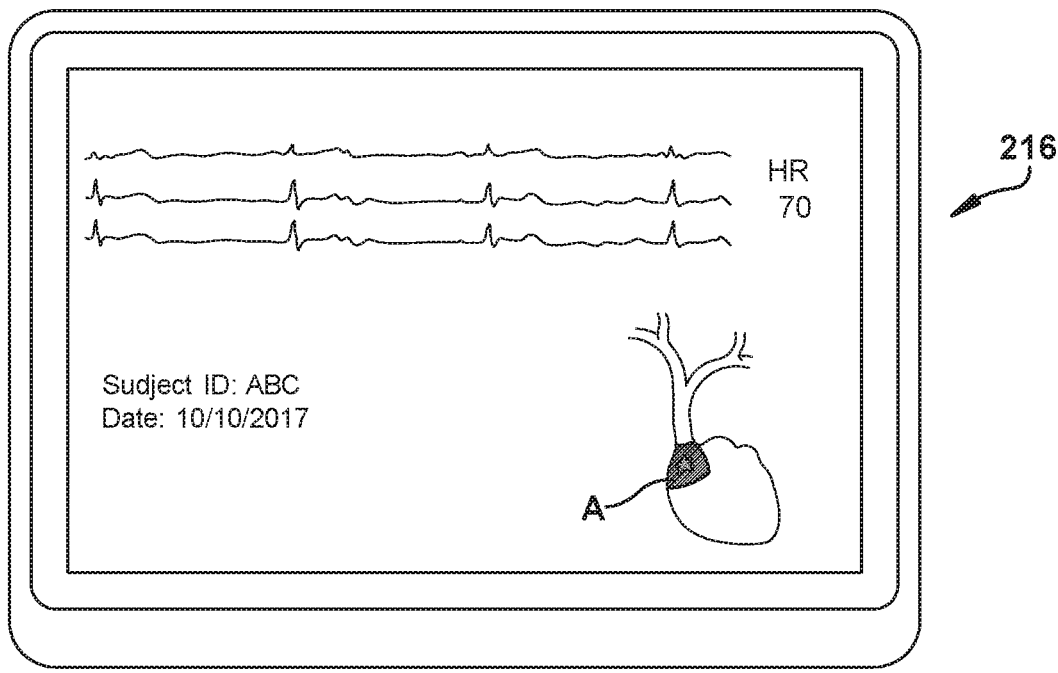
Figure 10:
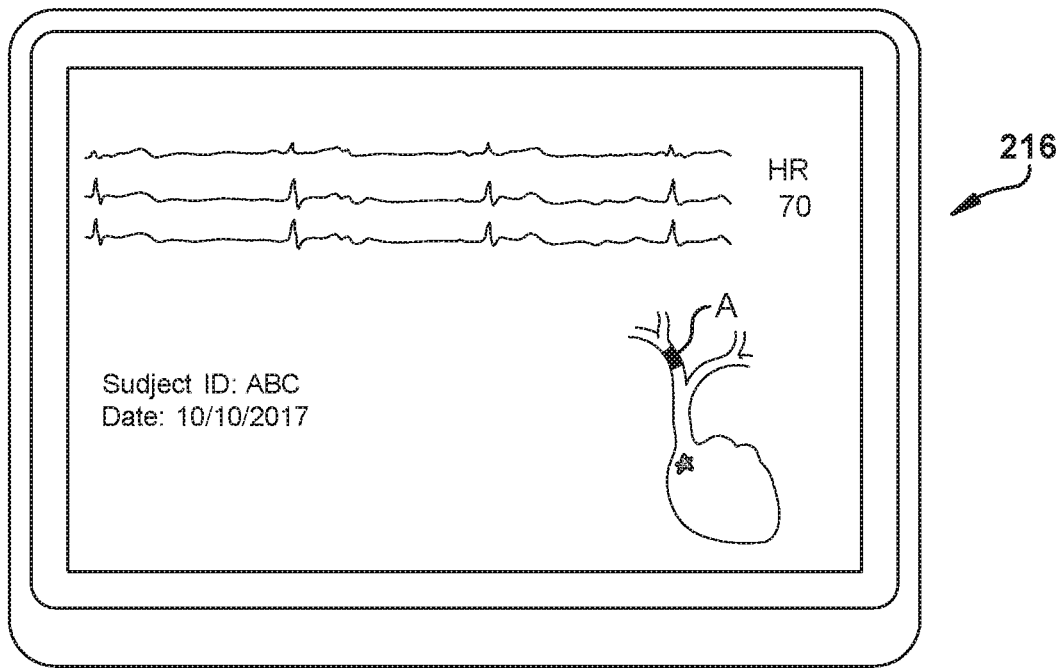

In FIG. 6, the stylet 100 is shown schematically as being inserted through the SVC and the CAJ, into the RA of the heart. As mentioned above with reference to use of the stylet 100 alone, the ECG readings taken by each of the bipolar stylet electrodes 108a and 108b, and the unipolar stylet electrodes 110, will differ at each of those distinct locations within the patient's heart. Accordingly, ECG readings from the bipolar stylet electrodes 108 and the unipolar stylet electrodes 110 can be used to verify or confirm insertion position similarly to the non-pad stylet 100 use described above, even in the system including the pads 328.

Stated differently, as the bipolar stylet electrodes 108 are placed in the RA, the unipolar stylet electrode 110a which is closest to the bipolar stylet electrodes 108 will be placed in the CAJ area and the unipolar stylet electrode 110b further from the bipolar stylet electrodes 108 will be located in the lower third of the SVC. By simultaneously monitoring one bipolar and two unipolar electrical activity signals of the cardiac system, the system can detect the locations within the cardiovascular system of the distal stylet end 106 and the adjacent parts of the stylet body 102. When a catheter 222 is slid over the stylet 100 and the catheter distal end 224 covers an electrode(s) 108, 110 of the stylet 100, the electrical signal(s) will be damped and the electrical signals which are referenced to the left leg LL pad 328 on the body surface will be substantially the same.

The system may include a user-perceptible display device 216 for communicating the position of the stylet electrode(s) 108/110 (and/or, by extension, the stylet 100 itself and/or the distal stylet end 106) within the patient's vasculature. An example user-perceptible display device 216 is shown in FIGS. 7-10. A schematic drawing of the patient's heart is shown, and a shaded area ("A") indicates the position of, for example, the distal stylet end 106 as triangulated by the system and/or as confirmed by ECG readings from the stylet electrode(s) 108/110. Here, as shown, the user-perceptible display device 216 can communicates the position of the stylet electrode(s) 108/110 (and/or, by extension, the stylet 100 itself and/or the distal stylet end 106) relative to a desired target position (the star, in FIGS. 7-10). By employing the user-perceptible display device 216, the "on-target" performance of the user is readily apparent, and the user has easy reference to steering and directional information which helps the stylet 100 insertion—and, by extension, the PICC or other catheter insertion—occur efficiently and accurately.

The above comments regarding the "stylet 100 alone" operation can also apply when the stylet 100 is part of an active or passive system—these are cooperative, not mutually exclusive, modes of operation. For example, the "pullback" placement of the stylet 100, the "signal damping" catheter position indication, or any other features of one system can be used with the other, as desired.

Figure 11:
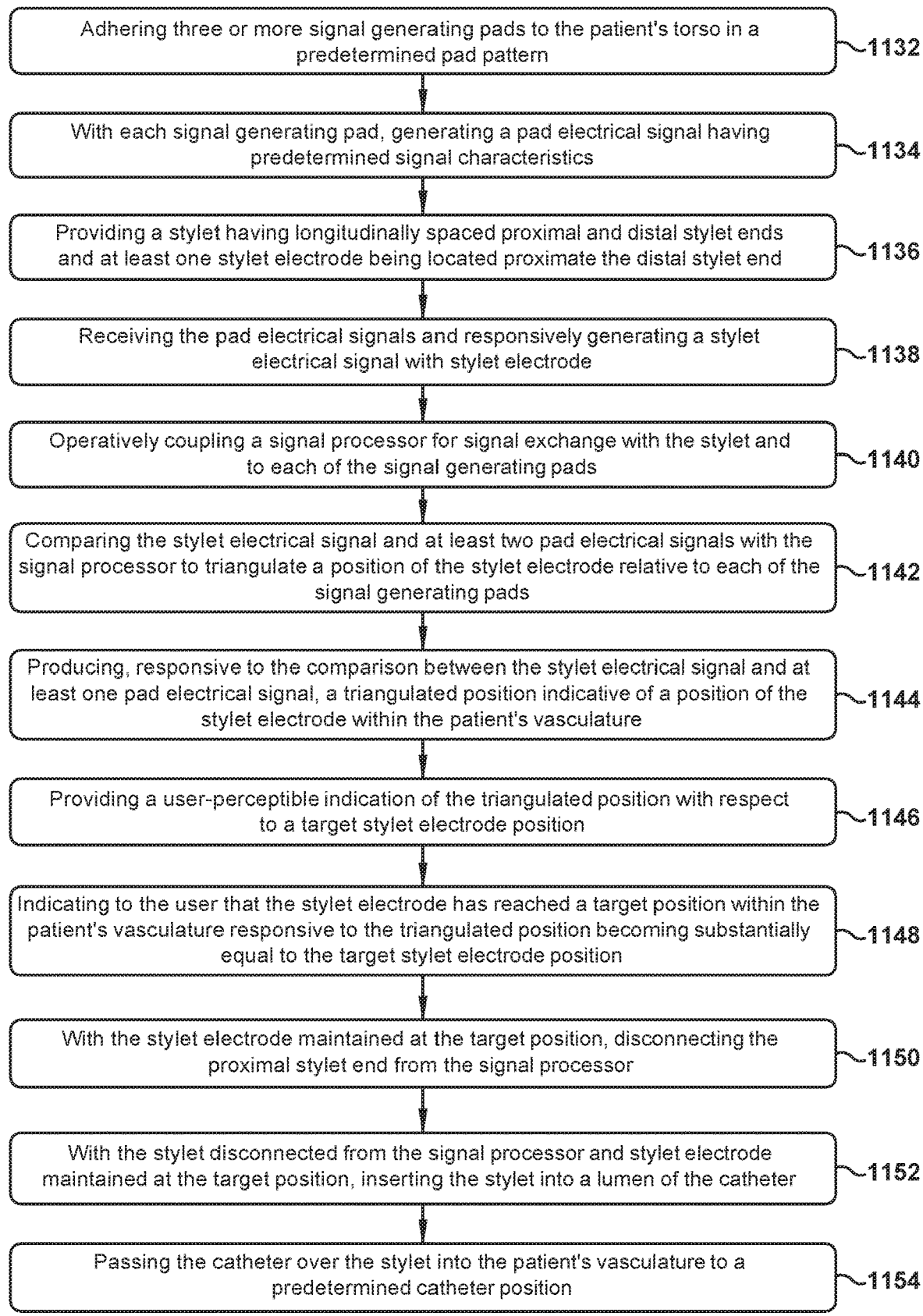
FIG. 11 is a flowchart of an example method of use of the apparatus of FIG. 1.

A method of placing a catheter within a patient's vasculature using the system and stylet 100 described herein is outlined, in part, in the flowchart of FIG. 11. However, any other desired steps or operations may be carried out during performance of the FIG. 11 flowchart steps, whether or not described or depicted herein. The catheter could be a central venous catheter, a peripherally inserted central catheter, or any other desired catheter or other elongate structure inserted into the cardiovascular system.

In first action block 1132 of FIG. 11, three or more pads 328 are adhered to the patient's torso 330 in a predetermined pad pattern—e.g., the five pads 328 can be adhered to the torso 330 in the X-shaped pattern described above. It is contemplated that the pads 328 could be adhered to the front/chest and/or the back of the patient's torso.

Control then passes to second action block 1134, wherein, with each pad, a pad electrical signal having predetermined signal characteristics (e.g., high frequency characteristics) is generated. This generation could include generating at least one of an intravascular electrocardiogram ("ECG") signal and an external ECG signal. This generation could also include generating a signal waveform having a predetermined frequency.

In third action block 1136, a stylet 100 having longitudinally spaced proximal and distal stylet ends 104 and 106, respectively, is provided. At least one stylet electrode 108/110 is located proximate the distal stylet end 106.

Progressing to fourth action block 1138, the pad electrical signals are received and a stylet electrical signal is responsively generated with the stylet electrode 108/110. That is, the bipolar and/or unipolar stylet electrodes 108 and 110 can be used to receive signals pertaining to intravascular cardiac activity (ECG, or passive system) and/or high frequency navigation signals (signal waveforms, or active system).

In fifth action block 1140, a signal processor is operatively coupled with the stylet 100 and to each of the pads 328 for signal exchange. Then, in sixth action block 1142, the stylet electrical signal and at least two pad electrical signals are compared by the signal processor to triangulate a position of the stylet electrode 108/110 relative to each of the pads 328. This comparison could include, in some implementations of the system, comparing the strengths of at least two pad electrical signals relative to the stylet electrical signal.

In seventh action block 1144, responsive to the comparison between the stylet electrical signal and at least one pad electrical signal, a triangulated position indicative of a position of the stylet electrode within the patient's vasculature is produced. When the stylet includes a plurality of stylet electrodes 108/110, each producing a stylet electrical signal, the step of seventh action block 1144 may also include producing, responsive to the comparison between each stylet electrical signal and at least one pad electrical signal, a triangulated position indicative of a position of each stylet electrode 108/110 within the patient's vasculature.

Control now proceeds to eighth action block 1146, where a user-perceptible indication of the triangulated position (of the stylet electrode 108/110) with respect to a target stylet electrode position is provided. Taking this concept a step further, and when multiple stylet electrodes 108/110 are provided, eighth action block 1146 could include indicating to a user, responsive to the position of each stylet electrode 108/110 within the patient's vasculature, a profile shape of at least a portion of the stylet 110 within the patient's vasculature.

Regardless of the type of indication provided, in ninth action block 1148, the system indicates to the user that the (or a particular) stylet electrode 108/100 has reached a target position within the patient's vasculature responsive to the triangulated position (as calculated) becoming substantially equal to the target stylet electrode position, when that happens. Location of the stylet electrode 108/110 at the target position may be verified by comparing the stylet electrical signal to a predetermined expected target position electrical signal, such as the ECG signal which would be expected when that stylet electrode 108/110 has reached the target position.

In tenth action block 1150, then, with the stylet electrode 108/110 maintained at the target position, the proximal stylet end is 104 disconnected from the signal processor 214.

Control then moves to eleventh action block 1152, wherein, with the stylet 100 disconnected from the signal processor 214 and the stylet electrode 108/110 maintained at the target position, the stylet 100 is inserted into a lumen 226 of the catheter 222.

At the end of the flowchart of FIG. 11, the catheter 222 is passed over the stylet 100 into the patient's vasculature, in twelfth action block 1154 to a predetermined catheter position.

Achievement of the predetermined catheter position by the catheter 222 could be verified via monitoring the stylet electrical signal for damping indicative of at least partial covering of the stylet electrode 108/110 with the catheter 222, as described above. The catheter distal end 224 location could be adjusted or fine-tuned through use of the stylet 100 to monitor at least one of the unipolar and bipolar electrical signals while the patient's arms are moved and/or breathing patterns are changed, as desired.

Once the catheter 222 is in the predetermined catheter position, the catheter 222 can be maintained in the predetermined catheter position as the stylet 100 is withdrawn in a proximal direction from the lumen 226 of the catheter 222. The PICC line installation, or other medical procedure for which the catheter 222 was placed, may then proceed as desired.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

I claim:

1. A system for determining a location of a structure within a patient's vasculature, the system comprising:
    three or more pads adhered to the patient's torso in a predetermined pad pattern, each pad being capable of generating a pad electrical signal having predetermined signal characteristics;
    a stylet having longitudinally spaced proximal and distal stylet ends, at least one stylet electrode being located proximate the distal stylet end, the stylet electrode being capable of receiving the pad electrical signals and responsively generating a stylet electrical signal; and
    a signal processor operatively coupled for signal exchange with the stylet and to each of the pads, the operative coupling between the signal processor and the stylet being a selective electrical coupling, the signal processor being capable of comparing the stylet electrical signal and at least two pad electrical signals to triangulate a position of the stylet electrode relative to each of the pads and responsively produce a triangulated position, the triangulated position being indicative of a position of the stylet electrode within the patient's vasculature;
wherein the triangulated position is calculated responsive to a comparison between the strengths of at least two pad electrical signals relative to the stylet electrical signal.

2. The system of claim 1, wherein at least one pad senses electrical heart activity and responsively generates an electrocardiogram ("ECG") signal as the pad electrical signal.

3. The system of claim 1, wherein at least one pad generates a signal waveform having a predetermined frequency.

4. The system of claim 1, including a user-perceptible display device for communicating the position of the stylet electrode within the patient's vasculature.

5. The system of claim 1, wherein the stylet includes a stylet body extending longitudinally between the proximal and distal stylet ends,
at least one stylet electrode is a bipolar stylet electrode located on the stylet body proximate the distal stylet end, the bipolar stylet electrode being capable of generating a stylet bipolar electrical signal responsive to sensed electrical activity within the patient's body;
at least one stylet electrode is a unipolar stylet electrode located on the stylet body, longitudinally interposed between the bipolar stylet electrode and the proximal stylet end, the unipolar stylet electrode being capable of generating a stylet unipolar electrical signal responsive to sensed electrical activity within the patient's body, and
the stylet includes at least two controller contacts located on the stylet body proximate the proximal stylet end, each controller contact being in electrical connection with a selected one of the bipolar stylet electrode and the unipolar stylet electrode, the at least two controller contacts being capable of selective electrical connection with a signal processor for transmitting a respective stylet bipolar electrical signal and stylet unipolar electrical signal to the signal processor.

6. The system of claim 5, wherein the at least one unipolar stylet electrode is two unipolar stylet electrodes spaced in the range of 0.5-2.5 cm apart.

7. The system of claim 5, wherein at least one of the unipolar stylet electrode and the bipolar stylet electrode is a platinum-iridium band extending circumferentially around the stylet body.

8. The system of claim 5, wherein the sensed electrical activity is naturally occurring cardiac electrical activity and the stylet unipolar and bipolar electrical signals are electrocardiogram ("ECG") signals.

9. The system of claim 5, wherein the sensed electrical activity is artificially imposed signal waveform electrical activity and the stylet unipolar and bipolar electrical signals are indicative of a strength of the signal waveform electrical activity at the respective unipolar or bipolar stylet electrode.

10. The system of claim 1, including five pads adhered to a patient's torso in an X-shaped pattern.

11. A stylet for sensing electrocardiac characteristics of a patient, the stylet comprising:
a stylet body with longitudinally spaced proximal and distal stylet ends;
at least one bipolar stylet electrode located on the stylet body proximate the distal stylet end, the bipolar stylet electrode being capable of generating a stylet bipolar electrical signal responsive to sensed electrical activity within the patient's body;
at least one unipolar stylet electrode located on the stylet body, longitudinally interposed between the bipolar stylet electrode and the proximal stylet end, the unipolar stylet electrode being capable of generating a stylet unipolar electrical signal responsive to sensed electrical activity within the patient's body; and
at least two controller contacts located on the stylet body proximate the proximal stylet end, each controller contact being in electrical connection with a selected one of the at least one bipolar stylet electrode and the at least one unipolar stylet electrode, the at least two controller contacts being capable of selective electrical connection with a signal processor for transmitting a respective stylet bipolar electrical signal and stylet unipolar electrical signal to the signal processor;
wherein the sensed electrical activity is artificially imposed signal waveform electrical activity and the stylet unipolar and bipolar electrical signals are indicative of a strength of the signal waveform electrical activity at the respective unipolar or bipolar stylet electrode.

12. The stylet of claim 11, wherein the at least one unipolar stylet electrode is two unipolar stylet electrodes spaced in the range of 0.5-2.5 cm apart.

13. The stylet of claim 11, wherein at least one of the at least one unipolar stylet electrode and the at least one bipolar stylet electrode is a platinum-iridium band extending circumferentially around the stylet body.

14. A system for determining a location of a structure within a patient's vasculature, the system comprising:
three or more pads adhered to the patient's torso in a predetermined pad pattern, each pad being capable of generating a pad electrical signal having predetermined signal characteristics;
a stylet having longitudinally spaced proximal and distal stylet ends, the stylet including a stylet body extending longitudinally between the proximal and distal stylet ends, at least one stylet electrode being located proximate the distal stylet end, the stylet electrode being capable of receiving the pad electrical signals and responsively generating a stylet electrical signal; and
a signal processor operatively coupled for signal exchange with the stylet and to each of the pads, the operative coupling between the signal processor and the stylet being a selective electrical coupling, the signal processor being capable of comparing the stylet electrical signal and at least two pad electrical signals to triangulate a position of the stylet electrode relative to each of the pads and responsively produce a triangulated position, the triangulated position being indicative of a position of the stylet electrode within the patient's vasculature;
wherein at least one stylet electrode is a bipolar stylet electrode located on the stylet body proximate the distal stylet end, the bipolar stylet electrode being capable of generating a stylet bipolar electrical signal responsive to sensed electrical activity within the patient's body;
wherein at least one stylet electrode is a unipolar stylet electrode located on the stylet body, longitudinally interposed between the bipolar stylet electrode and the proximal stylet end, the unipolar stylet electrode being capable of generating a stylet unipolar electrical signal responsive to sensed electrical activity within the patient's body, and
wherein the stylet includes at least two controller contacts located on the stylet body proximate the proximal stylet end, each controller contact being in electrical connection with a selected one of the bipolar stylet electrode and the unipolar stylet electrode, the at least two controller contacts being capable of selective electrical connection with a signal processor for transmitting a respective stylet bipolar electrical signal and stylet unipolar electrical signal to the signal processor, the sensed electrical activity being artificially imposed signal waveform electrical activity and the stylet unipolar and bipolar electrical signals being indicative of a strength of the signal waveform electrical activity at the respective unipolar or bipolar stylet electrode.

15. The system of claim 14, wherein at least one pad senses electrical heart activity and responsively generates an electrocardiogram ("ECG") signal as the pad electrical signal.

16. The system of claim 14, wherein at least one pad generates a signal waveform having a predetermined frequency.

17. The system of claim 14, including a user-perceptible display device for communicating the position of the stylet electrode within the patient's vasculature.

18. The system of claim 14, wherein at least one of the unipolar tylet electrode and the bipolar stylet electrode is a platinum-iridium band extending circumferentially around the stylet body.

19. The system of claim 14, wherein the sensed electrical activity is naturally occurring cardiac electrical activity and the stylet unipolar and bipolar electrical signals are electrocardiogram ("ECG") signals.

20. The system of claim 14, wherein the triangulated position is calculated responsive to a comparison between the strengths of at least two pad electrical signals relative to the stylet electrical signal.

\* \* \* \* \*